United States Patent [19]

Hattori et al.

[11] Patent Number: 5,604,128
[45] Date of Patent: Feb. 18, 1997

[54] **ISOLATED CULTURES OF *PESTALOTIOPSIS FUNEREA* IFO 5427 AND *PESTALOTIOPSIS NEGLETA* FERM BP-3501**

[75] Inventors: Atsushi Hattori; Masami Miura; Mitsuyo Takahashi; Noriyoshi Uchida, all of Tokyo; Kouhei Furuya; Tsuyoshi Hosoya, both of Isukuba, all of Japan

[73] Assignee: Sankyo Company, Limited, Tokyo, Japan

[21] Appl. No.: 461,421

[22] Filed: Jun. 5, 1995

Related U.S. Application Data

[62] Division of Ser. No. 410,931, Mar. 27, 1995, which is a division of Ser. No. 363,580, Dec. 22, 1994, which is a continuation of Ser. No. 123,588, Sep. 17, 1993, abandoned, which is a continuation of Ser. No. 928,879, Aug. 11, 1992, abandoned.

[30] Foreign Application Priority Data

Aug. 13, 1991 [JP] Japan ................................. 3-202771

[51] Int. Cl.$^6$ ............................ C12N 1/14; C12N 1/16; C12N 9/34
[52] U.S. Cl. ...................... 435/254.1; 435/205; 435/911
[58] Field of Search ........................ 435/254.1, 911, 435/205

[56] References Cited

U.S. PATENT DOCUMENTS

| | | | |
|---|---|---|---|
| 3,660,236 | 5/1972 | Dworschack et al. | 435/96 |
| 4,247,637 | 1/1981 | Tamura et al. | 435/96 |
| 4,254,225 | 3/1981 | Tamura et al. | 435/96 |
| 4,318,989 | 3/1982 | Marshall | 435/205 |
| 4,536,477 | 8/1985 | Katkocin et al. | 435/205 |
| 4,587,215 | 5/1986 | Hirsh | 435/96 |
| 4,591,560 | 5/1986 | Kainuma et al. | 435/96 |
| 4,604,352 | 8/1986 | Zeikus et al. | 435/42 |
| 4,605,619 | 8/1986 | Horwath et al. | 435/94 |
| 4,628,031 | 12/1986 | Zeikus et al. | 435/205 |
| 4,727,026 | 2/1988 | Sawada et al. | 435/96 |
| 4,782,143 | 11/1988 | Morehouse et al. | 536/102 |
| 4,840,900 | 6/1989 | Wasileski | 435/96 |
| 4,863,864 | 9/1989 | Ashikari et al. | 435/205 |
| 4,898,822 | 2/1990 | Asada et al. | 435/121 |
| 5,188,956 | 2/1993 | Nanmori et al. | 435/200 |

FOREIGN PATENT DOCUMENTS

| | | |
|---|---|---|
| 0171218 | 2/1986 | European Pat. Off. . |
| 0185327 | 6/1986 | European Pat. Off. . |
| WO83/01458 | 4/1983 | WIPO . |
| 86/01831 | 3/1986 | WIPO . |

OTHER PUBLICATIONS

T. Takahashi et al, "Different Behavior towards Raw Starch of Three Forms of Glucoamylase from a Rhizopus Sp.", Sep. 1985, pp. 663–671, Journal of Biochemistry, vol. 98, No. 3.

H. C. Dube, "Studies on the Nutrition of the Genus Pestalotiopsis. II. Chromatographic Analysis of the Medium During Utilization of Various Carbohydrates", Mycopathologica et Mycologia Applicata, Aug. 6, 1971, pp. 347–353, vol. 44, No. 4, Aug. 6, 1971.

R. A. B. Verma et al., "Utilization of Carbohydrates by Three Fungi Imperfecti Causing Leaf Spot Diseases of Mahogany", 1975, pp. 317–321, Indian Phytopathology. vol. 28.

H. Sasaki et al, "Screening of Microorganisms for Raw Starch Saccharifying Enzyme Production", Jun. 1986, pp. 1661–1664, Agricultural and Biological Chemistry, vol. 50, No. 6.

Hayashida et al, "High Concentration–Ethanol Fermentation of Raw Ground Corn", Agr. Biol. chem. 46, 1947–1950 (1982).

Abe et al, "Raw–Starch Digesting Enzymes of aspergillus sp. K–27" J. Jpn. Soc. Starch Science, 32, 128–135 (1985).

Ishigami, "Raw Starch–Digesting Amylase from Chalara paradoxa", J. Jpn. Soc. Starch Science, 34, 66–74 (1987).

Taniguchi et al, "Characterization of a Potato Starch–digesting Bacterium and Its Production of Amylase", Agr. Biol. Chem. 46, 2107–2115 (1982).

Mizokami et al, "Crystallization and Properties of Ra Starch Hydrolyzing Enzyme Product by *Streptococcus bovis*", Nogei–kagaku Kaishi 51, pp. 299–307 (1977).

Jeda et al, "Multiple Forms of Glucoamylase of Rhizopus Species", Die Starke, 27, 123–128 (1975).

*Primary Examiner*—David M. Naff
*Assistant Examiner*—L. Blaine Lankford
*Attorney, Agent, or Firm*—Frishauf, Holtz, Goodman, Langer & Chick

[57] ABSTRACT

Isolated cultures of *Pestalotiopsis funerea* IFO 5427 and *Pestalotiopsis neglecta* FERM BP-3501 are provided. The cultures produce a glucoamylase which digests starch.

2 Claims, 3 Drawing Sheets

ISOLATED CULTURES OF *PESTALOTIOPSIS FUNEREA* IFO 5427 AND *PESTALOTIOPSIS NEGLETA* FERM BP-3501

This is a division of application Ser. No. 08/410,981, filed Mar. 27, 1995, which is a division of application Ser. No. 08/363,580 filed Dec. 22, 1994, which is a continuation of application Ser. No. 08/123,588 filed Sep. 17, 1993 (abandoned), which is a continuation of application Ser. No. 07/928,879 filed Aug. 11, 1992 (abandoned).

The present invention relates to an enzyme which is capable of hydrolysing or digesting various polysaccharides, particularly starch, and provides methods for the production of said enzyme, as well as methods and compositions using the enzyme.

Starch, the carbohydrate reserve material of most plants, is formed from two substances, amylose and amylopectin. Amylose, which is the inner and relatively soluble portion of starch granules, comprises a linear chain of D-glucopyranose units, linked in an α-1,4 fashion, whilst amylopectin, which is the outer and relatively insoluble portion of starch granules, is a hexosan, a polymer of glucose.

Starch makes up more than half of the carbohydrate ingested by humans, and, when it has been well cooked for use as a food, is rapidly hydrolysed in the human body. However, starch is also an important industrial starting material, which may be broken down by hydrolysis to release monosaccharides and oligosaccharides, the latter being sugars containing two or more monosaccharide units, which are themselves extremely important and have many uses in various fields. For example, the resulting sugars may be fermented to give alcohol, which may be used as such (for example, sake is produced in this way) or may provide a valuable source of renewable energy.

In the industrial enzymatic hydrolysis of starch, it has hitherto been necessary first to cook the starch until it breaks down into its constituent components, and only then subject it to the enzymatic hydrolysis. However, this step is expensive in terms of consumption of energy, and it also results in the production of an unpleasant odour.

It is known that various microorganisms produce enzymes which are capable of hydrolysing oligo- and poly- saccharides such as starch, and enzymes have been isolated, in particular, from fungi and bacteria. A number of enzymes are known to decompose starch, and some of these form the basis of traditional industries, such as the sake brewing industry. However, these traditional enzymes are only effective on cooked starch, and so the raw (i.e. uncooked) starch must first be boiled to cook or gelatinise it prior to the enzymatic reaction. This is a substantial disadvantage of these enzymes, as it adds an extra process step and increases energy consumption of the process as a whole, whilst also, as noted above, producing an unpleasant odour. It would, therefore, be desirable to find enzymes which can hydrolyse raw (i.e. uncooked) starch. A further advantage of an enzyme capable of digesting raw starch is that it could lead to the production of new alcoholic drinks based on tradional drinks but with different flavors as a result of the use of a variety of uncooked starch sources. Furthermore, a limited reaction of such an enzyme on flour would lead to an improvement in the quality of flour-based foodstuffs, such as doughs (e.g. bread, cake or pizza doughs) or noodles.

Efforts have, therefore, been made to provide enzymes capable of hydrolysing raw starch. Bacteria such as those belonging to the Bacillus species and *Streptococcus bovis*, for example, are known to produce enzymes capable of hydrolysing raw starch and known as α-amylases. α-Amylase hydrolyses the internal α-1,4 linkages in the amylose and amylopectin components of starch to yield maltose, maltotriose and α-dextrin. Of these, maltose is a disaccharide, i.e. it consists of two glucose residues; maltotriose is a trisacccharide, i.e. it consists of three glucose units; and α-dextrin consists of several glucose units joined by a variety of linkages. Another class of enzymes which may be used to decompose raw starch is known as "the glucoamylases". Glucoamylase is an enzyme capable of hydrolysing oligo- and poly- saccharides comprising glucose sub-units which are joined by linkage of α-1,4 and α-1,6, into the individual glucose units, stepwise from the non-reducing terminus of the saccharide chain. Such an enzyme has been isolated from various fungal species, for example fungi belonging to the genus Rhizopus, as well as, for example, *Aspergillus awamori*, Aspergillus K-27 and *Chalara paradoxa*. The production of these enzymes and their activity is described by, for example, Ueda et al. [Starke 27, 123 (1975)], Hayashida et al. [Agr. Biol. Chem. 46, 1947 (1982)], Abe et al. [Starch Science 32, 128 (1985)], Ishigami et al. [Starch Science 32, 136 (1985)], Taniguchi et al. [Agr. Biol. Chem. 46, 2107 (1982)], and Mizokami et al. [Nogeikagaku Kaishi 51, 299 (1977)].

However, although these α-amylase and glucoamylase enzymes have demonstrated the ability to hydrolyse raw starch, it has been found that their activity is not very high, and, moreover, they are unstable and have a very restricted pH range within which they are active. They have not, therefore, been usable for the industrial hydrolysis of starch and of other oligo- and poly- saccharides.

We have now discovered an enzyme which is capable of hydrolysing raw or uncooked starch, and which possesses stability and activity characteristics which overcome the problems associated with known enzyme preparations.

The enzyme of the present invention is an enzyme which is capable of hydrolysing uncooked starch, which enzyme has an optimum pH for this activity of from 4 to 5 and which is stable at a temperature of 37° C. within the pH range of from 3 to 9.

The present invention also provides a method for the production of an enzyme capable of hydrolysing uncooked starch, which method comprises cultivating a fungus of the genus Pestalotiopsis and isolating the enzyme from the resulting culture.

The present invention further provides a process for decomposing uncooked polysaccharides, especially starch, using the enzyme of the present invention.

The invention is further illustrated by the following drawings, in which.

The enzyme of the present invention is classified as a glucoamylase and can be characterised by the following properties.

1. The enzyme has an optimum pH of 4 to 5 and exhibits maximum activity at a pH of about 4.5, as can be seen from FIG. 1.

2. The enzyme has a molecular weight of about 82,000 daltons, as determined by sodium dodecyl sulphate polyacrylamide gel electrophoresis. We have not obtained the enzyme in the form of crystals, and so its crystal structure has not been determined.

3. The enzyme is stable within a pH range of from 3 to 9, preferably from 3 to 10, at ordinary temperatures, e.g. from 10° to 60° C., especially about 37° C., as is demonstrated in FIG. 2 of the accompanying drawings, but it is inactivated at pH values below 3 and above 10. In contrast, the enzyme produced by *Aspergillus K-27*, which is thought to be the most active of the prior art enzymes referred to above, is only stable at pH values in the range of from 4.0 to 7.1, and, in general, none of the prior art enzymes is thought to be stable at alkaline pH values.

4. The thermal stability of the enzyme will depend on the presence or absence of other substances and on the nature of any such substances. For example, the enzyme, when in solution in a 20 mM acetate buffer (pH 4.5), is inactivated at temperatures exceeding 60° C. When a substrate, for example starch, is also present in the solution, the thermal stability of the enzyme may be increased and it is inactivated at a temperature between 65° C. and 70° C.

Figure 3:
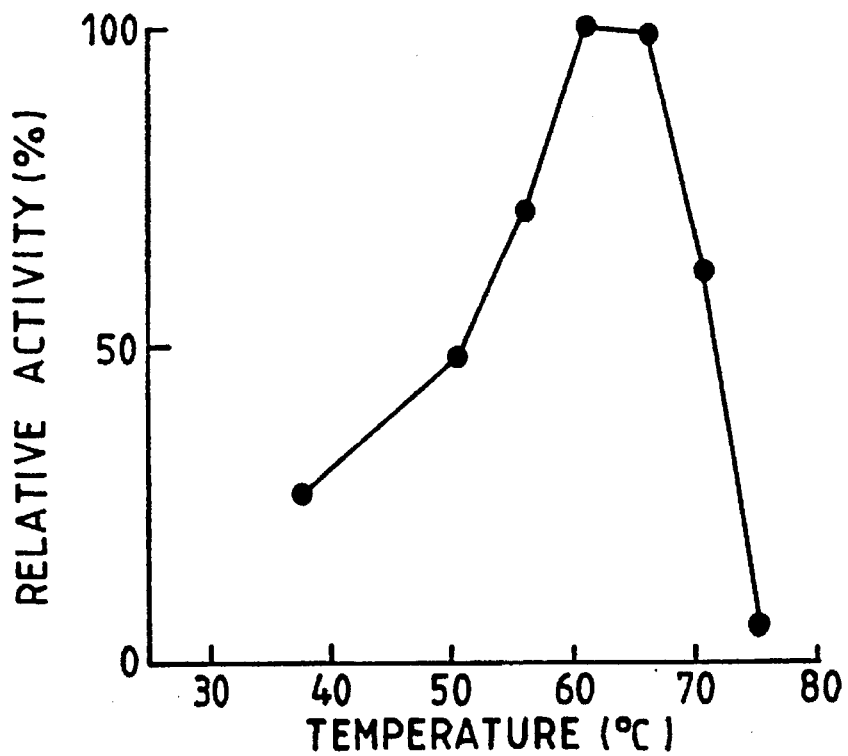
FIG. 3 shows the temperature/activity curve for the enzyme of the invention.

5. The enzyme is active within a temperature range of from 10° C. to 75° C. The optimum temperature is found to be within a range of from 20° C. to 65° C., and the maximum activity can be observed near 60° C., as can be seen from FIGS. 3 and 4.

6. The enzyme is not inhibited by multi-valent metal ions, such as mercury, lead or iron ions, and there is no change in activity in the presence of ethylenediamine tetraacetate.

The glucoamylase of the present invention acts on a variety of polysaccharide substrates, especially starch, to release glucose and/or other reducing sugars. A reducing sugar is a mono- or oligo- saccharide having a potential aldehyde group. The enzyme is capable of hydrolysing the α-1,4 and α-1,6 bonds formed between monosaccharide units in polysaccharides to release glucose units. Examples of substrate polysaccharides which may be hydrolysed by the glucoamylase of the present invention include starch itself, as well as amylopectin, amylose, maltose, maltotriose, isomaltose, oligosaccharides comprising maltose units (i.e. malto-oligosaccharides), oligosaccharides comprising iso-maltose units (i.e. isomalto-oligosaccharides) and dextran. The glucoamylase of the present invention is particularly characterised by its ability to hydrolyse starch. It is able to act on both of the two components of starch, amylose and amylopectin, by hydrolysing the bonds beginning from the non-reducing terminals of these molecules at intervals of a glucose unit. The polymers are substantially completely broken down into individual glucose units. It acts in a similar way on malto-oligosaccharides. It can release two glucose molecules from maltose. Its activity on isomaltose is, although weak, decomposition, resulting in the formation of two glucose molecules. It also acts on isomalto-oligosaccharides and dextran, and hydrolyzes starting from their non-reducing terminals at intervals of a glucose unit.

Starch is the preferred substrate for the glucoamylase of the present invention. The starch may be obtained from any natural or synthetic source, for example tubers and grains, and in particular rice, wheat, corn, potato and sweet potato. Of the starch sources that we have investigated, rice is the best source of hydrolysable starch for the enzyme, and, when starch from rice is contacted with the enzyme, the starch is substantially totally hydrolysed into individual glucose units. The following Table shows the amount of glucose formed after treatment of each of these starch sources for 30 minutes with an enzyme solution which is the culture broth described hereafter in Example 1. The results are shown as relative amounts, taking the glucose production from corn as 100.

TABLE 1

| Substrate | Glucose production |
|---|---|
| Rice | 128 |
| Wheat | 110 |
| Corn | 100 |
| Sweet potato | 85 |
| Potato | 27 |

The glucoamylase of the present invention will hydrolyse starch in any form. Thus, for example, the starch may be raw or it may be cooked, and the starch may be purified or in its native form. The enzyme of the present invention is, however, particularly suited for use in the hydrolysis of raw starch and it is an unexpected advantage of the present invention that it may be used for, and shows a high activity towards, the hydrolysis of raw starch rather than requiring that the starch be cooked first.

The present invention also provides a method for the production of the glucoamylase of the present invention which method comprises cultivation of a fungus of the genus Pestalotiopsis which is capable of producing the glucoamylase of the present invention under conditions suitable for the production of said enzyme, and isolation of said enzyme from the culture medium.

The glucoamylase of the present invention can be isolated from a fungus of the genus Pestalotiopsis. Although other genera of fungi do produce enzymes of this type, all those enzymes which we have investigated are only active for the digestion of cooked, not raw, starch. In particular, the enzyme can be isolated from one of the following Pestalotiopsis strains:

*Pestalotiopsis funerea* IFO 5427 (SANK 15174),

*Pestalotiopsis microspora* IFO 31056,

*Pestalotiopsis acaciae* IFO 31054,

*Pestalotiopsis crassiusla* IFO 31055; or

*Pestalotiopsis neglecta* (SANK 13390).

Of the fungi mentioned above, *Pestalotiopsis microsporo* IFO 31056, *Pestalotiopsis acaciae* IFO 31054, and *Pestalotiopsis crassiusla* IFO 31055 were all known before the priority date hereof and are all freely obtainable from the Institute for Fermentation in Osaka (IFO), Japan.

*Pestalotiopsis neglecta* (SANK 13390) and *Pestalotiopsis funerea* IFO 5427 (SANK 15174) are newly isolated microorganisms and have been deposited in accordance with the provisions of the Budapest Treaty on 7th Aug. 1991 at the Fermentation Research Institute, Agency of Industrial Science and Technology, Japan and given the accession numbers FERM BP-3501 and FERM BP-3502 respectively. Both SANK 13390 and SANK 15174 were deposited on Aug. 7, 1991. SANK 13390 was given accession no. FERM BP-3051 and SANK 15174 was given accession no. FERM BP-3052. *Pestalotiopsis funerea* IFO 5427 (SANK 15174) has also been deposited at the Institute for Fermentation (IFO) in Osaka, Japan, under the IFO accession number 5427.

*Pestalotiopsis funerea* IFO 5427 (SANK 15174) is the preferred microorganism from which the enzyme of the present invention is isolated.

The mycological properties of the two fungal species *Pestalotiopsis funerea* IFO 5427 (SANK 15174) and *Pestalotiopsis neglecta* (SANK 13390) have been determined using conventional techniques and are as follows.

WSH Medium, which was used in these experiments, has the following composition:

| | |
|---|---|
| Oat Meal | 10 g |
| KH$_2$PO$_4$ | 1 g |
| MgSO$_4$.7H$_2$O | 1 g |
| NaNO$_3$ | 1 g |
| Agar | 20 g |
| Water | to 1000 ml |

*Pestalotiopsis funerea* IFO 5427 (SANK 15174), after cultivation at 23° C. for 7 days, produces a colony on WSH medium (which has the composition shown above) which is white in colour and which has a surface covered with a cotton-like mycelium. There are a large number of black, viscous and drop-like conidial piles, each containing many conidia.

Each conidium ranges from 23 µm to 28 µm in length and from 6.5 µm to 0.5 µm in width. Each conidium consists of an appendage hypha and a clavate spindle structure, which is straight and constricted at the septal wall. This latter region consists of a total of 5 cells. The central part of the conidium comprises three coloured cells, each about 16 µm in length, which are sandwiched between transparent cells found at the top and bottom of the conidium. The transparent cells at the top of the conidium are cone shaped and generally have either 2 or 3 transparent appendange hyphae per cell. These hyphae are generally all of the same length, for example from 20 µm to 30 µm, and they all have simple tips. The transparent cells at the bottom of the conidium are also cone shaped and each transparent cell has one basal appendage hypha, of from 5 µm to 7 µm in length, and with a simple tip.

The three central coloured cells are a brown colour, and they are all of approximately the same colour. However, the uppermost two cells can sometimes be a slightly deeper colour than the remaining cell.

These properties were compared to the properties of known Pestalotiopsis species and were found to be in accordance with the properties of *Pestalotia funerea* Desmazieres, described in "Monograph of Monochaetia and Pestalotia" by E. F. Guba, and published by Harvard University Press in 1961. Furthermore, it was found that this species had already been classified as Pestalotiopsis, as demonstrated by R. L. Steyaert in "Contribution I' etude monographique de Pestalotia de Not. et Monochaetia Sacc. (Truncatla gen. nov. et Pestalotiopsis gen. nov.)", Bull. Jard. Bot. Brux. 19, 285–358 (194). The fungal species described by Steyaert is known as *Pestalotiopsis funerea* (Desm) Steyaert. From a comparison of the properties of the fungus *Pestalotiopsis funerea* IFO 5427, employed in the present invention, it was confirmed that this fungus is a new strain of the same species as *Pestalotiopsis funerea* (Desm) Steyaert.

*Pestalotiopsis neglecta* (SANK 13390) was first isolated by us from the needle leaves of the Japanese cedar tree, sugi, in 1989. Its mycological properties were determined using conventional techniques and are as follows.

Colonies of *Pestalotiopsis neglecta* (SANK 13390), when grown on WSH medium (having the composition as indicated above) at 23° C. for 7 days, are white in colour with a surface covered with a cotton-like mycelium. There are a large number of black, viscous and drop-like conidial piles, each containing many conidia.

Each conidium ranges from 21 µm to 29 µm in length and from 5.0 µm to 6.5 µm in width. Each conidium consists of an appendage hypha and a spindle structure, which is straight or slightly curved and constricted at the septal wall. This latter region consists of a total of 5 cells. The central part of the conidium comprises three coloured cells, each about 13 µm to 16 µm in length, which are sandwiched between transparent cells found at the top and bottom of the conidium. The transparent cells at the top of the conidium are cone shaped and generally have either 2 or 3 transparent appendange hyphae per cell. These hyphae are generally all of the same length, for example from 14.5 µm to 25.5 µm, and they all have simple tips. The transparent cells at the bottom of the conidium are also cone shaped and each transparent cell has one basal appendage hypha, of from 3 µm to 8 µm in length, and with a simple tip.

The three central coloured cells are a brown colour, and they are all of approximately the same colour. However, the uppermost two cells can sometimes be a slightly deeper colour than the remaining cell.

These properties were compared to the properties of known Pestalotiopsis species and were found to be in accordance with the properties of *Pestalotia neglecta* Thuem., described in "Monograph of Monochaetia and Pestalotia" by E. F. Guba, and published by Harvard University Press in 1961. Furthermore, it was found that this species had already been classified as Pestalotiopsis, as demonstrated by R. L. Steyaert in "New and Old Species of Pestalotiopsis", Transactions of the British Mycological Society 36, 81–89 (1953). The fungal species described by Steyaert is known as *Pestalotiopsis neglecta* (Thuem.) Steyaert. From a comparison of the properties of the fungus *Pestalotiopsis neglecta* (SANK 13390) described in the present invention, it was confirmed that this fungus is a strain of the same species as *Pestalotiopsis neglecta* (Thuem.) Steyaert.

It has been established that the glucoamylase of the present invention is produced by each of *Pestalotiopsis funerea* IFO 5427 (SANK 15174), *Pestalotiopsis microspora* IFO 31056, *Pestalotiopsis acaciae* IFO 31054, *Pestalotiopsis crassiusla* IFO 31055 and *Pestalotiopsis neglecta* (SANK 13390). However, as is well known, the properties of fungi can vary considerably and such fungi can readily undergo mutation, both through natural causes and as the result of induction by artificial means (for example, ultraviolet irradiation, radioactive irradiation, chemical treatment, etc.). Accordingly the present invention embraces the use of any microorganism which can be classified within the genus Pestalotiopsis and which shares with the strains mentioned above the ability to produce the glucoamylase of the present invention. The mutant strains also include any strains obtained by genetic engineering techniques, for example, recombination, transduction, transformation or the like. It is a matter of simple experimentation to determine, on the basis of the information given herein regarding the properties of the glucoamylase of the present invention, whether any given strain produces this compound or produces it in sufficient quantity to render that strain of potential commercial interest.

The glucoamylase of the present invention may be produced by the culture of any one of the above strains of fungus in culture media of the type conventionally used for the production of other similar products from similar microorganisms. Such media necessarily contain micro-biologically assimilable sources of carbon and of nitrogen as well as inorganic salts, as is well known to those skilled in the art. The minimum requirement for the medium will be that it contains those ingredients essential for the growth of the microorganism.

Suitable carbon sources include, for example: glucose, fructose, maltose, sucrose, mannitol, glycerol, dextrin, oatmeal, rye, starch (for example corn starch or potato starch), potato, corn powder, soybean meal, cottonseed oil, molasses, citric acid and tartaric acid, any of which may be employed alone or in combination with any one or more others. Typical amounts will be in a range from about 1 to 10% w/v of the amount of medium, although the amount may be varied as desired and in accordance with the desired result.

Suitable nitrogen sources include any substance containing a protein, for example, or other readily assimilable source of nitrogen. Representative examples of nitrogen sources are organic nitrogen sources from animals and plants, and may be extracts from such natural sources as soybean meal, wheat bran, peanut meal, cottonseed meal, cottonseed oil, casein hydrolysate, fermamine, fish meal, corn steep liquor, peptone, meat extract, yeast, yeast extract and malt extract; and such inorganic nitrogen sources as sodium nitrate, ammonium nitrate and ammonium sulphate. As with the carbon source, these may be employed alone or in any combination. Suitable amounts are typically within a range from about 0.1 to 6% w/v of the amount of medium.

Suitable nutrient inorganic salts are those which provide trace elements as well as the major constituent of the salt. Preferably, salts should provide such ions as sodium, ammonium, calcium, phosphate, sulphate, chloride and carbonate. Such trace metals as potassium, cobalt, manganese, iron, magnesium and strontium, or salts capable of providing such ions as bromide, fluoride, borate or silicate ions, may also be present. Examples of specific salts include monopotassium phosphate, dipotassium phosphate and magnesium sulphate.

The process of the present invention may be carried out either by a liquid or solid culture technique, using methods well known in the art. The pH of the medium for the liquid culture for producing the glucoamylase of the present invention, by cultivation of any one of the Pestalotiopsis species described herein, more preferably strains SANK 15174 and 13390, preferably varies within the range of from 3.0 to 7.0, optionally from 4.5 to 7.0.

The cultivation may be carried out at any temperature at which the fungus is active, preferably a temperature within the range of from 20° C. to 40° C., although a temperature of from 25° C. to 32° C. is more preferred. The period over which culture takes place is not fixed and will vary depending on various factors, for example the composition of the medium, the temperature at which cultivation is performed, the pH and the rate of aeration. We have found that a culture period of from 3 to 10 days is sufficient, although from 4 to 8 days is preferred.

The glucoamylase of the present invention is produced under aerobic culture conditions and conventional aerobic culture methods, such as solid culture, liquid culture, shaking culture and aeration-stirring (submerged) culture methods, may be used. In the case of small scale cultivation, shaking culture for 7 days at 28° C. is typical. The culture may take place in a single step, i.e. the culture may be initiated by inoculation of a medium sterilised by conventional means, for example by heating to 121° C., and cultivation for the determined period is followed by harvesting. If desired, the above-mentioned cultivation may be preceded by a seed culture step in order to provide sufficient cells for the subsequent production step. If employed, the seed culture may be carried out under the same conditions as described above.

After completion of the cultivation, the desired glucoamylase of the present invention, which is present in the liquid phase of the culture broth, can be fractionated by filtering off the mycelium and any other solid material, perferably using diatomaceous earth as a filter aid, or by centrifugation. The enzyme, which is then present in the filtrate or in the supernatant, can then be recovered by extraction and can be purified by conventional means. Alternatively, the culture broth as such may be used for the enzymatic digestion of starch without any specific isolation of the enzyme as such, and this may be preferred as eliminating several purification steps.

For example, one purification procedure comprises the following steps. First, the culture liquid is filtered to remove fungal cells. The supernatant is collected and is subjected to ultrafiltration and, after condensation by evaporation under reduced pressure, the salt concentration and pH are adjusted so that they are equal to those values for a 20 mM acetate buffer (pH 4.5). The resulting solution is subjected to column chromatography, for example using a Mono Q column (Mono Q is a trade name for a product of Pharmacia, Sweden) and with a 20 mM acetate buffer as eluent and the glucoamylase of the present invention is obtained in a substantially pure form.

The activity of the enzyme may be determined in accordance with two enzyme assays.

1. Assay for Raw Starch Hydrolysis

The first assay determines the ability of the enzyme to hydrolyse raw starch, and the amount of enzyme activity required to produce 1 μmol of glucose per minute of reaction time is regarded as one unit of enzyme activity.

0.5 g of potato starch and 0.1 ml of an enzymatic solution, produced as described in Example 1 hereafter, are added to 0.9 ml of a 20 mM acetate buffer (pH 4.5). The reaction mixture is stirred until it is homogeneous and is then allowed to stand at 37° C. for 60 minutes. After this time, 10 μl of the reaction mixture is removed and the amount of glucose within the sample is quantitatively determined using high performance liquid chromatography on, for example, a Shodex DC-613 column ("Shodex" is a trade name) with a 65:35 by volume mixture of acetonitrile and water as the eluting solvent.

2. Assay to Determine Reducing Sugar Formation

The second assay determines the amount of reducing sugar formed by the enzymatic hydrolysis of starch. The amount of enzyme activity required to form an amount of reducing sugar corresponding to 1 μmol of glucose per minute of reaction time is regarded as one unit of enzyme activity.

0.25 ml of the enzymatic solution prepared as described in Example 1 was added to 0.5 ml of a 4% w/v solution of starch in a 0.1M acetate buffer (pH 4.5), and the reaction mixture was allowed to stand for 30 minutes at 37° C. At the end of this time, 0.1 ml of the reaction mixture was removed and was added to 0.9 ml of water. The amount of reducing sugar contained in the sample was then determined according to the method of Nelson-Somogyi [M. Somogyi, J. Biol. Chem. 160, 61 (1945)].

The glucoamylase of the present invention is useful in the hydrolysis of polysaccharides. Accordingly the present invention also provides a process for the hydrolysis of a polysaccharide substrate which comprises contacting said substrate with The glucoamylase of the present invention.

The enzyme is preferably contacted with the substrate in an aqueous medium. For example, the substrate may be suspended in an aqueous medium or merely moistened with such a medium. The enzyme itself is preferably employed in an aqueous medium. There is no need to provide especially purified water, and water may be employed straight from the well or tap. For more effective enzymatic reaction, an acid (for example acetic acid), an alkali (for example sodium hydroxide) or a buffer solution (for example an acetate buffer) may be added to adjust its pH to the desired value within the range of activity of the enzyme. A pH value within the range of from 4 to 7 is preferred, a value within the range of from 4.5 to 5.5 being more preferred. For example, in an acetate buffer solution, the best activity is seen when the pH is 4.5, as is demonstrated in FIG. 1.

The substrate employed may be, for example, the starch contained in grains such as rice, wheat or corn, or in rhizomic plants such as sweet potatoes or potatoes. We prefer that the substrate concentration in the reaction medium should be from 1 to 50% by weight.

As described above, the temperature at which the enzyme is active may vary widely, depending on many factors, and the preferred reaction temperature for the hydrolysis reaction will, of course, depend on this. However, we generally prefer to carry out the reaction at a temperature of from 10° C. to 75° C., more preferably from 20° C. to 65° C. and most preferably from about 30° C. to 60° C. The time required for the reaction may also vary widely, depending on many factors, such as the nature of the substrate, the reaction temperature and the pH employed, but, under the preferred conditions outlined above, a period of from 10 minutes to 10 days (more preferably from 6 hours to 5 days) will usually suffice.

After completion of the enzymatic reaction, the glucose-containing product thus obtained can be used directly for further processing treatment without any intermediate separation of the glucose itself. Alternatively, the product can be used directly after filtering off any insoluble matter by any conventional means. Alternatively, a glucose solution of any required concentration can be obtained by condensation, with or without first subjecting the product to any of these separation procedures. In addition, the product can be also obtained, if necessary, by addition of water, followed by extraction with a water-immiscible organic solvent further followed by distilling the organic solvent off. Then, if necessary, the product can be further purified by any conventional means such as column chromatography and recrystallization.

The preparation of the enzyme of the present invention is further illustrated by the following non-limiting Examples, and the subsequent Test Example illustrates the activity of the enzyme of the invention.

EXAMPLE 1

Isolation from *Pestalotiopsis funerea*

1. Culture 80 ml of a culture medium having the composition shown below and having a pH of 3.5, were charged into a 500 ml culture flask. The medium was sterilised by heating to a temperature of 121° C. and maintainenance at this temperature for 20 minutes. After sterilisation and cooling, the medium was inoculated with one loopful of the fungus *Pestalotiopsis funerea* IFO 5427 (SANK 15174), and the inoculated medium was cultured at 28° C. for 7 days and at 210 rpm (a rotation radius of 35 mm), using a rotary shaker.

The culture medium employed had the following composition:

| | |
|---|---|
| corn starch: | 1.5% |
| corn steep liquor: | 1.0% |
| cotton seed grains: | 1.0% |
| (brand Pharmamadia, which is a trade name for a product of Traders Oil Mill) | |
| monopotassium phosphate: | 0.5% |
| magnesium sulphate.7H$_2$O: | 0.25% |
| water | to 100% |

(percentages are by weight based on the final volume).

2. Isolation (i) After the fungus had been cultured as described above, the culture medium was centrifuged at 5000×G, to break down and sediment the cells of the fungus, and the resulting sediment was separated from the supernatent, to give 50 ml (equivalent to 32 units/ml in the reducing sugar assay and 4.5 units/ml in the raw starch hydrolysis) of an enzyme solution. The enzyme in solution after this purification stage was found to have the following properties.

1. Optimum pH for activity: 4.5.
2. pH range at which stable: pH 3 to pH 9.
3. Optimum temperature for activity: 60° C.
4. Temperature range at which stable: up to 60° C.

These values do not change substantially with further purification of the enzyme solution, as may be seen from the properties indicated hereafter.

(ii) The enzyme solution obtained in step 2(i) above was further purified by the following steps. The solution was subjected to ultrafiltration and was then condensed to one third of its original volume by evaporation under reduced pressure. Sufficient dilute acetic acid solution was then added to adjust the salt concentration and pH of the enzyme solution until it reached values equivalent to those for a solution of a 20 mM acetate buffer (pH 4.5). As a result of these steps, 15 ml of enzyme solution were obtained.

(iii) 2 ml of the solution obtained in accordance with step 2(ii) above, containing 40 units/ml in the reducing sugar assay, were removed and were then further purified by column chromatography using a Mono Q Column (a trade name for a product of Pharmacia) and gradient elution. The eluting solvent consisted of a 20 mM acetate buffer (pH 5) having a salt concentration ranging from 0 to 0.2M. After chromatography 2 ml of the enzyme having glucoamylase activity were obtained (having an activity of 15 units/ml in the reducing sugar assay and 3.5 units/ml in the raw starch hydrolysis).

Figure 1:
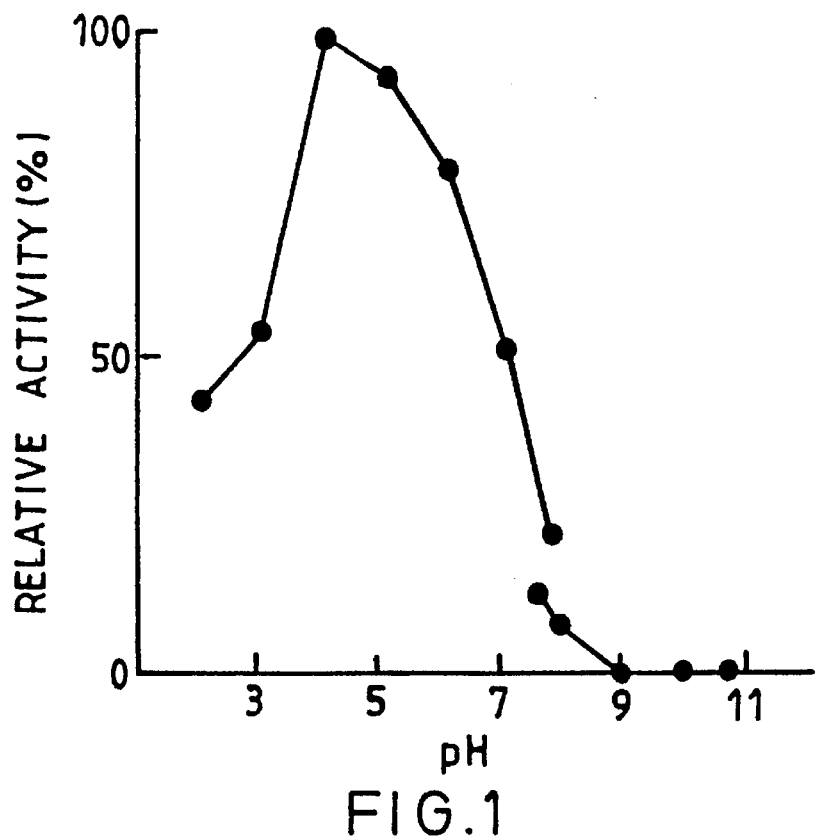
FIG. 1 shows the pH-activity curve for the enzyme of the present invention.
Figure 2:
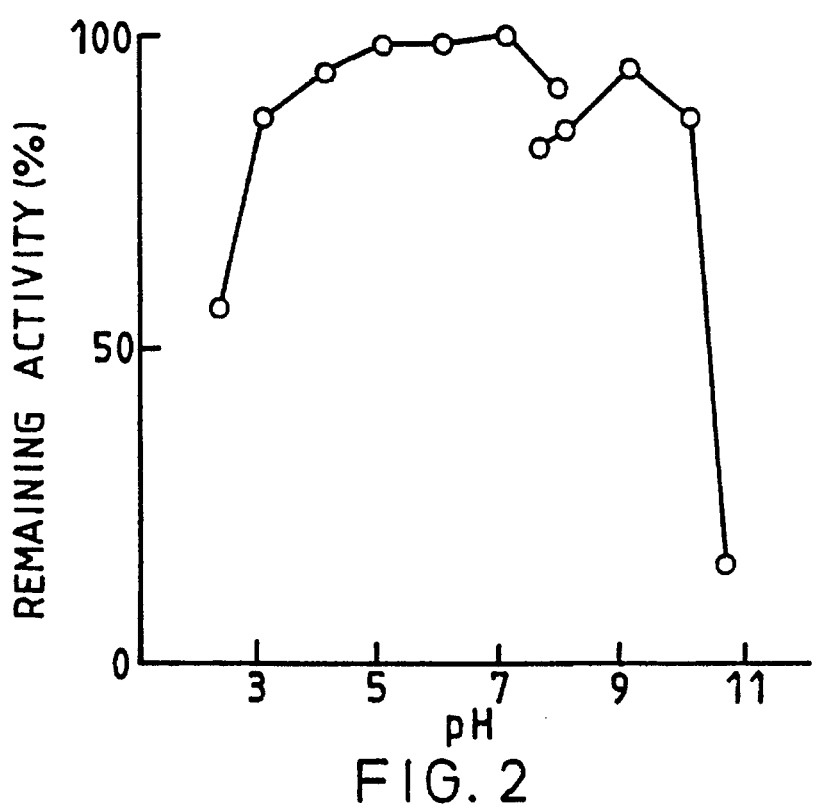
FIG. 2 shows the relationship between pH and stability of the enzyme of the invention.
Figure 4:
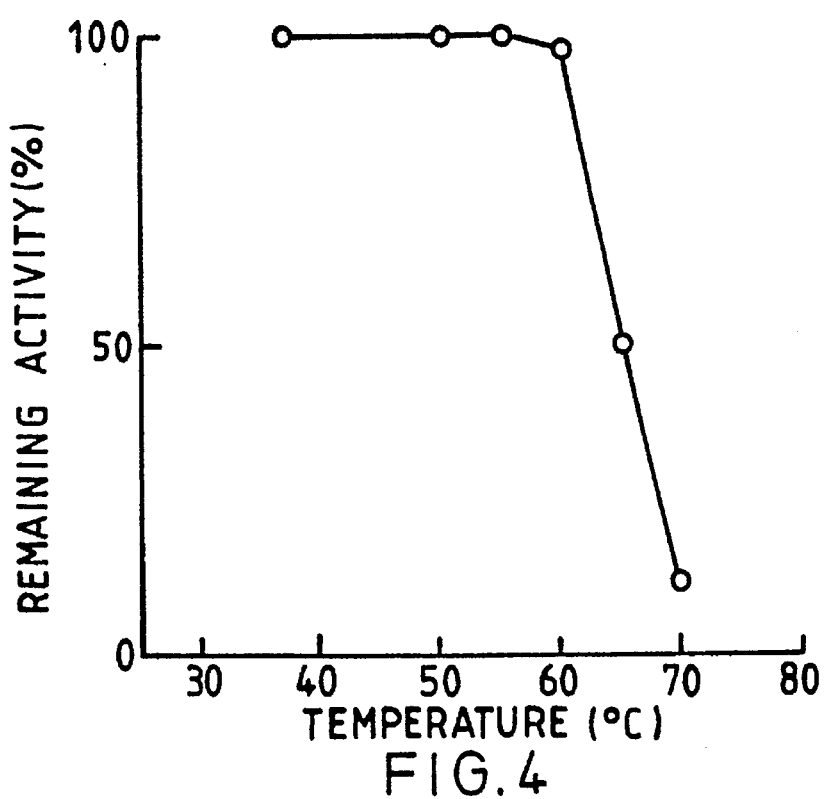
FIG. 4 shows thermal stability of the enzyme of the invention.

The enzyme thus obtained also had the following properties:

1. Molecular weight: approximately 82,000 daltons using sodium dodecyl sulphate polyacrylamide gel electrophoresis.
2. Optimum pH for activity: pH 4 to pH 5. FIG. 1 of the accompanying drawings shows the relationship between pH and enzymatic activity.
3. pH range at which stable: pH 3 to pH 10. FIG. 2 of the accompanying drawings shows the relationship between remaining enzymatic activity and pH at the time of the treatment, after heating the enzyme at 37° C. for 1 hour.
4. Optimum temperature for activity: 60° C. to 65° C. FIG. 1 of the accompanying drawings shows the relationship between temperature and enzymatic activity.
5. Temperature range at which stable: up to 60° C. FIG. 4 of the accompanying drawings shows the relationship between remaining enzymatic activity and temperature at the time of the treatment, after heating the enzyme at a pH value of 4.5 for 1 hour.

EXAMPLE 2

Isolation from *Pestalotiopsis funerea*

1. Culture 5 g of wheat grains and 5 ml of water were added to a 100 ml Erlenmeyer flask, and the resulting medium was sterilised by heating at 121° C. for 30 minutes. After sterilisation and cooling, the medium was inoculated with one loopful of *Pestalotiopsis funerea* IFO 5427 (SANK 15174) and the inoculated medium was cultured while allowing the seeds to germinate (i.e. under malting conditions) for 7 days at 30° C.

Isolation

After completion of the culture period, 50 ml of water were added to the flask with stirring. The insoluble matter was then filtered off, and 35 ml of a solution containing enzyme were obtained. This solution had an activity of 2.4 units/ml in the reducing sugar assay and 0.28 units/ml in the raw starch hydrolysis assay.

EXAMPLE 3

Isolation from Other Pestalotiopsis Sources

Following a procedure substantially as set out in Example 1 above, except that the initial pH of the medium was adjusted to 6.0, and using, in turn, *Pestalotiopsis microspora* IFO 31056, *Pestalotiopsis acaciae* IFO 31054, *Pestalotiopsis crassiusla* IFO 31055 or *Pestalotiopsis neglecta*, SANK 13390 instead of *Pestalotiopsis funerea* to inoculate the sterilised medium, an enzyme solution containing the enzyme of the invention was obtained.

The activities of the enzymes produced in this Example in the assays for determination of raw starch hydrolysis and reducing sugar formation described above are as follows:

| Source Strain | raw starch hydrolysis (units/ml) | reducing sugar formation (units/ml) |
| --- | --- | --- |
| *Pestalotiopsis microspora* | 0.30 | 4.6 |
| *Pestalotiopsis crassiusla* | 0.54 | 6.8 |
| *Pestalotiopsis acaciae* | 0.22 | 3.0 |
| *Pestalotiopsis neglecta* | 0.35 | 5.6 |

TEST EXAMPLE 0.5 g of each of the following sources of raw starch were added to 0.9 ml of a 20 mM acetate buffer (pH 4.5), to produce 5 separate reaction mixtures.

Starch Sources: potato, sweet potato, corn, wheat and rice.

0.1 ml of the purified enzyme preparation obtained as described in Example 1 was added to each of the above five reaction mixtures. The mixtures were stirred until they reached homogeneity and then they were allowed to stand at 37° C. for 24 hours. At hourly intervals 10 μl of each reaction mixture was removed and the amount of glucose determined by high performance liquid chromatography on a Shodex DC-613 ("Shodex" is a trade name) chromatography column, using a 65:35 by volume mixture of acetonitrile and water as the eluent.

Figure 5:
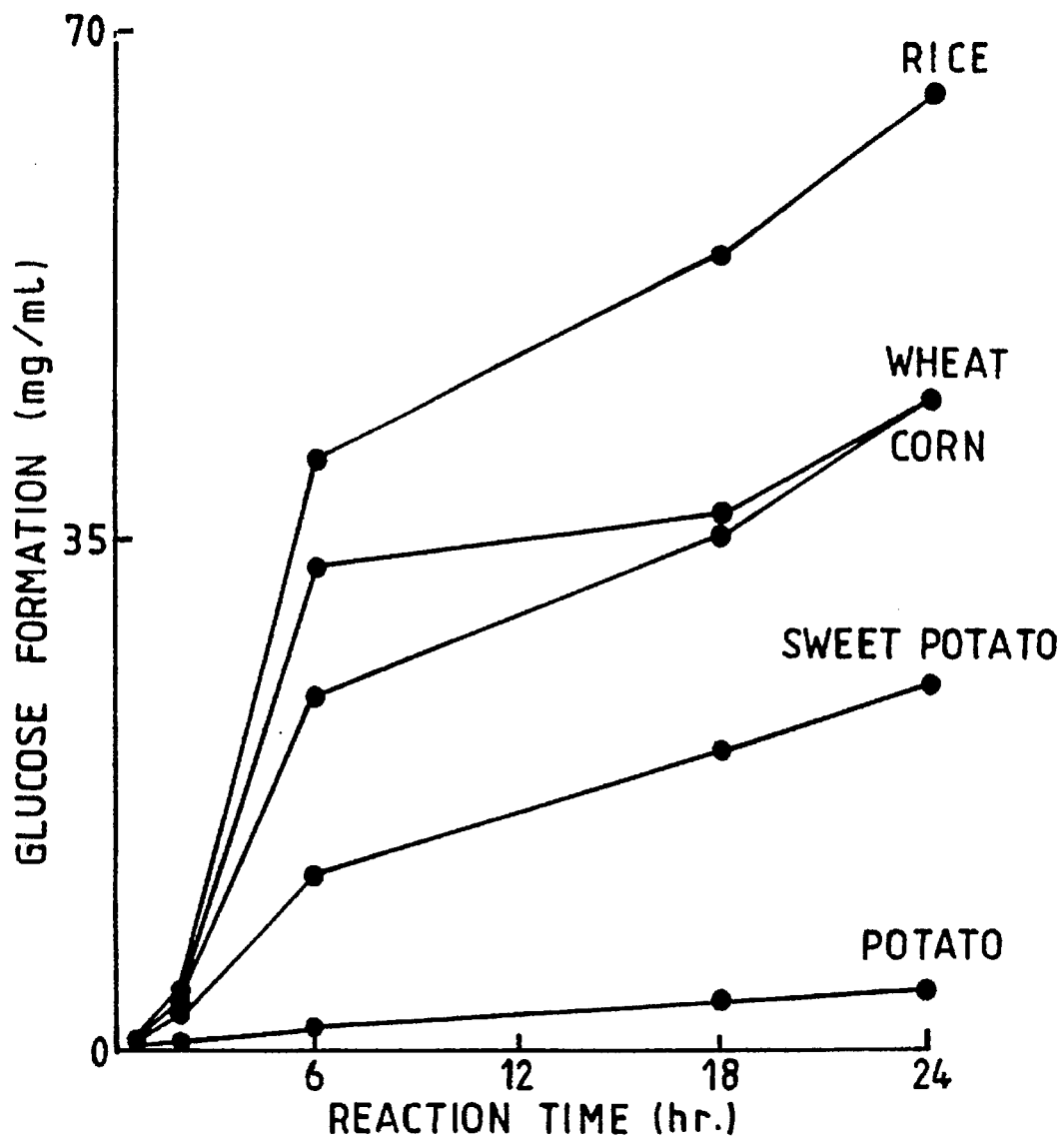
FIG. 5 shows the activity of the enzyme in hydrolysing raw starch from various sources.

The results are shown in FIG. 5 of the accompanying drawings.

We claim:

1. A biologically pure culture of *Pestalotiopsis funerea* IFO 5427.

2. A biologically pure culture of *Pestalotiopsis neglecta* FERM BP-3501.

* * * * *